United States Patent [19]

Guirguis

[11] Patent Number: 5,224,489
[45] Date of Patent: Jul. 6, 1993

[54] URINE TESTING MODULE WITH CYTOLOGY CUP

[75] Inventor: Raouf A. Guirguis, Rockville, Md.

[73] Assignee: La Mina Ltd., Rockville, Md.

[21] Appl. No.: 749,108

[22] Filed: Aug. 23, 1991

Related U.S. Application Data

[63] Continuation of Ser. No. 553,585, Jul. 18, 1990, Pat. No. 5,042,502, which is a continuation-in-part of Ser. No. 411,041, Sep. 22, 1989, Pat. No. 4,953,561.

[51] Int. Cl.⁵ ............................................. A61B 5/00
[52] U.S. Cl. .................................... 128/771; 604/404
[58] Field of Search ................ 128/760, 762, 771; 604/318, 404; 422/56, 60

[56] References Cited

U.S. PATENT DOCUMENTS

| | | | |
|---|---|---|---|
| 3,774,455 | 11/1973 | Seidler et al. | 128/771 |
| 4,040,791 | 8/1977 | Kuntz | 128/762 |
| 4,473,530 | 9/1984 | Villa-Real | 128/762 |
| 4,557,274 | 12/1985 | Cawood | 128/760 |
| 4,573,983 | 3/1986 | Annis | 128/760 |
| 4,827,944 | 5/1989 | Nugent | 128/771 |

*Primary Examiner*—Max Hindenburg
*Attorney, Agent, or Firm*—John S. Hale

[57] ABSTRACT

The present invention is directed toward an apparatus and a method which can use immunoassay in sample treatment apparatus for diagnostic and testing purposes of urine by concentrating specific urine antigen in a small volume area and concentrating the urinary sediments in a separate small volume area. Urine is transported through the tubular container under pressure to flow through the sample container which screens off the urinary sediments and the beads so that antigens carried in the urine are collected and concentrated on the beads.

3 Claims, 1 Drawing Sheet

URINE TESTING MODULE WITH CYTOLOGY CUP

RELATED CASES

This application is a continuation application of U.S. patent application Ser. No. 07/553,588 filed Jul. 18, 1990, now U.S. Pat. No. 5,042,502, which is a continuation-in-part of Ser. No. 07/411,041 filed Sep. 22, 1989, now U.S. Pat. No. 4,953,561.

BACKGROUND OF THE INVENTION

The present invention is directed to medical and laboratory fluid specimen collecting and testing apparatus, and more specifically to an apparatus for detecting the presence of specific antigens in a biological fluid such as urine and collecting urinary sediments from the urine.

Under normal conditions, urine contains a small number of cells and other particulate matter shed from the entire length of the urinary tract. These materials are usually known as urinary sediments. Typical urinary sediments consist of red blood cells, white blood cells, epithelial cells, casts, mucus and crystals. In addition, sporatic urinary sediment such as bacteria, yeast, parasites and spermatozoa occur in patients suffering from various types of disorders or engaging in particular activities. Examination of urinary sedimentation is a routine procedure in urinanalysis. With disease, these cells as well as other formed elements are often increased and may help to localize the site and type of injury. For example, excessive numbers of red blood cells may indicate tumor, stones or imflammation. Excessive number of leukocytes may indicate infection or other inflammatory disease. In contrast to the hypocellular nature of normal urine, neoplastic cells (e.g., transitional, squamous and columnar cells) are shed more frequently in malignant conditions of the bladder epithelium.

Immunoassay works upon the simple principle that is the specific recognition of an antigen by an antibody. Thus specific antigen detection and quantification requires an antibody which recognizes the uniqueness of an antigen. The antigen binding site of antibodies recognizes about six amino acids or their equivalent in mass. One unique binding site serves as an identifying marker for that protein.

When a definitive antibody for a given antigen is available it is used to identify the antigen in the sample mixture. Once the antibody combines with the antigen a means is needed to recognize the resulting complex. There presently exists a need to concentrate antigens from volumes of fluid when the antigen is not present in measurable quantities in specific fluid volumes.

It is generally necessary in diagnosing and testing for many diseases to collect biological fluids from a patient. Although blood, urine and cerebrospinal fluids are the most common specimens received for diagnosis, other fluids such as seminal, synovial, pleural, pericardial, peritoneal, amniotic and sweat fluids are associated with specific conditions and diseases. It is important during the collection handling of biological fluid specimens that the potential of specimen deterioration, contamination and the spread of any infection from the specimen be minimized. While urine is commonly collected in 100 ml containers, the actual urine testing is commonly conducted with relatively small amounts of sample around 0.2-0.5 ml in volume. Thus because of the small test quantity, cancer producing antigen can only be ascertained after the cancer is in an advanced or late tumor stage. The rest of the urine sample is used for further testing, frozen or is thrown away. Additional problems occur in shipment when dealing with urine because of the relatively large volume of fluid involved in the collection specimen samples. There is also the risk of sample deterioration because of the relatively short sample shelf life of urine unless kept in specific temperature conditions. In addition there is also the potential for specimen damage or spillage during the collection and/or shipment process as well as the potential for destruction of certain molecular components of the specimen such as antigens contained therein as well as cellular materials such as urinary sediments, because the packaging does not protect the urine or causes chemical changes in the different components which will negate the test results or result in false data being obtained when the specimen is tested.

There currently exists a need to concentrate molecular components of urine and separately concentrate the urinary sediments for diagnosing the presence of cancer at an early stage in the development of the cancer.

A typical specimen collecting apparatus is shown by U.S. Pat. No. 4,741,346. This apparatus includes a base stand which supports the specimen vial in an upright position. A funnel is inserted in the open end of the specimen vial and surrounds and encloses the upper portion of the vial. The base stand has an upwardly extending tubular wall which at least partially surrounds the vial in connection with the cap and allows the user to remove the vial without touching the surface or coming in contact with the specimen. Examples of various types of liquid containers for collecting and transporting urine are shown by U.S. Pat. Nos. 3,777,739; 3,881,465; 4,042,337; 4,084,937; 4,244,920; 4,492,258 and 4,700,714.

Another specimen collection device shown by U.S. Pat. No. 4,040,791 discloses a collection receptacle having a nipple upon which is mounted a specimen container which receives a predetermined amount of the specimen in a sealed condition. The specimen container is provided with an integally formed cap which is placed over the opening in which the collector nipple is inserted. U.S. Pat. No. 4,557,274 discloses a midstream urine collector having a funnel which transmits urine into a cup member which is covered by a membrane cover.

A combined strip testing device and collection apparatus is shown by U.S. Pat. No. 4,473,530 and is directed to an apparatus which integrates testing and collection by having chemical reagent test strips present within the tube together with specific gravity reading means allowing immediate testing of the urine. U.S. Pat. No. 4,573,983 is directed towards a liquid collection system having an antiseptic member on the discharge section which uses a filter of air and bacteria impervious material to filter the urine.

It is therefore desirable to provide an easy to handle disposable apparatus and method which transports a fluid sample such as urine through a specific immobilized antibody bead bed to capture a concentrated amount of antigen and urinary sediments from the urine allowing more sensitive cancer detection from the sample while also providing that the test specimen can be compactly stored for a period of time in concentrated form allowing cancer testing to be performed quickly and accurately by distal testing facilities.

BRIEF SUMMARY OF THE INVENTION

The invention is directed toward a urine antigen and cellular component collection system. The shuttle system offers a relatively simple method to separate the cellular components or urinary sediments of the urine sample from its soluble substances and also provides an easy way to concentrate and partially purify the antigens in the urine sample. Filtration is essential to remove particulate matter in the urine sample that may interfere with the antigen-antibody reaction. The concentration and partial purification of the urine help enrich the antigen concentration and remove other substances that may compete with their antibody binding sites. The inventive device is in the form of a removable sealable urinary sediment/antigen specimen container having two separated chambers with primary monoclonal antibodies covalently bound to beads positioned in one chamber and an adjacent chamber separated from the first chamber by a filter membrane designed to contain urinary sediments of the urine sample. The urine is pumped by a syringe through the container where it engages and passes through the filter, having a 5 micron filter particle size, which screens cells and cell debris into the urinary sediment chamber while allowing passage of filtered urine fluid and associated antigen through the antibody bead chamber. The immobilized antibody beads are carried by the urine away from the bead bed into the buffered urine held in the syringe. The beads have specific monoclonal antibodies covalently bound thereto to capture specific antigen carried by the urine fluid. The urine was previously buffered to a neutral pH so that it remains in a stable preserved state and prelabelled polyclonal antibodies are added to the urine after it has been buffered and before it is pumped through the container.

The buffered urine sample is drawn into the syringe and emptied and filled several times after which the bead container is washed in coloring reagent and the color developed on the beads is then read using a reflectometer.

It is thus an object of the invention, particularly where ligands such as antigens are being removed from the body fluids for testing to collect and concentrate specific antigens from the urine and to collect cells and other particulate matter in a separate compartment. Previously such testing has been accomplished by a series of tests involving a number of different containers and expensive laboratory equipment of a limited sensitivity.

In the accompanying drawings, there is shown an illustrative embodiment of the invention from which these and other of objectives, novel features and advantages will be readily apparent.

DETAILED DESCRIPTION OF THE INVENTION

Figure 1:
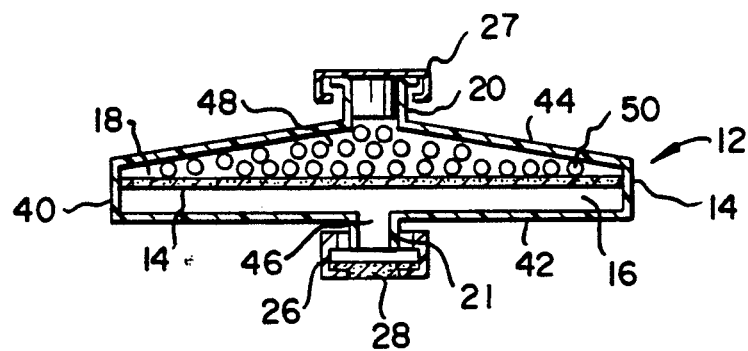
FIG. 1 is a cross sectional schematic view of the inventive shuttle apparatus.
Figure 2:
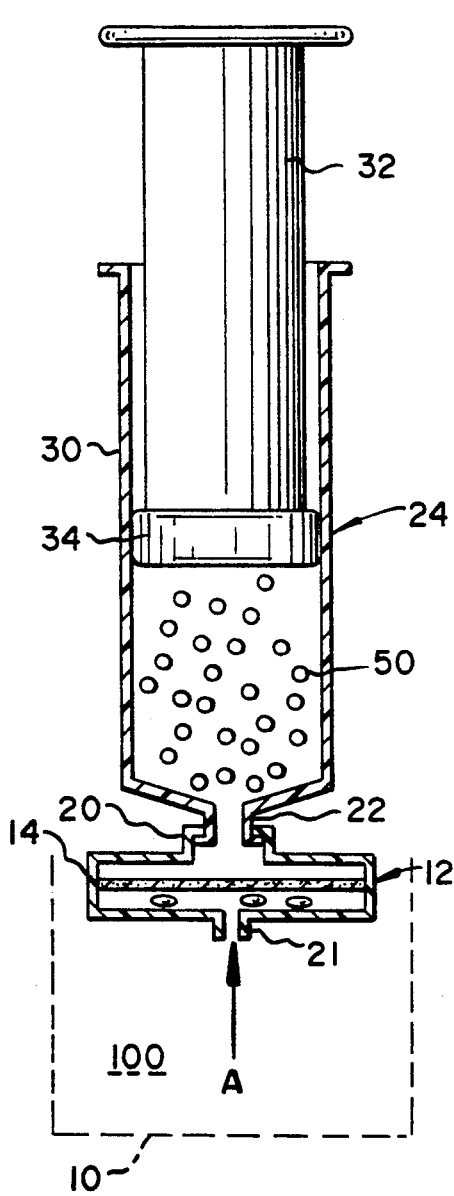
FIG. 2 is a cross sectional schematic view of the shuttle apparatus mounted in a syringe showing the shuttle immersed in buffered urine with the buffered urine entering the syringe with direction of movement shown by arrow A.

The preferred embodiment and best mode of the invention is seen in FIGS. 1 through 4. The initial collection of the urine is normally housed in a graduated 100 ml container 10 as shown in phantom in FIGS. 2 and 3. Such a container is currently manufactured by Becton Dickerson Labware under the designation 4013 specimen container. This collection container holds 4.5 oz. (approx. 133 ml) and is graduated with a polyethylene snap lid. A beads and urinary sediment shuttle container 12 with treatment filter 14 mounted therein divides the container into separate chambers 16 and 18. The filter 14 preferably has a filter particle size of 5 microns but can range from 1-5 microns or any size which is suitable to allow fluid flow with antigens to pass therethrough but also prevent the passage of beads 50 and urinary sediments. The container shuttle 12 can be a disposable sterile single use filter assembly manufactured by Gelman Sciences with a 5 VM filter. Any suitable filter can be used in the container housing 13 such as the aqueous glass microfiber filter manufactured by Xydex, a subsidiary of Genex Corporation or a membrane member manufactured by Millipore Corporation. One end 20 of the container is fitted with a threaded projection which is adapted to fit onto the luer lock 22 of a 30 cc syringe 24, manufactured by Becton Dickinson & Co. It should be noted that any pump type device could be used in place of the syringe 24 as for example an autovial spunglass filter manufactured by Genex Corporation. The syringe 24 has a barrel 30 with associated leur lock 22, piston 32 and piston head 34. While the invention can be used for any body fluid it is primarily designed for use in collecting concentrated urine antigen and urinary sediments for use in testing for various kinds of cancer in the body and determines the presence and stage of the cancer.

As shown in FIGS. 1 through 4 the beads shuttle container 12 is constructed of polystyrene. The container housing 13 has an exterior cylindrical wall 40 with end walls 42 and 44 respectively defining a urine entrance port 46 as further defined by end conduit 21 and exit port 48 as further defined by end conduit 20. The interior of the shuttle container 12 contains a membrane filter 14 mounted therein with a filter size ranging from 0.5 to 5 microns. The filter 14 divides the interior of the container housing 13 into two chambers 16 and 18. A bed of beads 50 with immobilized antibodies bound thereto is positioned in chamber 18 on the syringe side of the filter 14.

A cell collection cup 26 is snap fit or threaded on end conduit 21 and the bottom wall 28 of the cup serves as a final screen filter.

The bead 50 are preferably visible (above 10 micron in diameter) so that their flow into the syringe barrel 30 and back to the container 12 can be visually observed to make sure of maximum bead contact with the urine. Monoclonal antibodies are immobilized (covalently bound) on beads 50 as is well known in the art and are designed to have binding sites which have a high affinity for the epitopes of the cancer antigens carried in the urine which have complexed with the prelabelled polyclonal antibodies as described below.

It should be noted that the volume of beads 50 should not be greater then the volume of the container chamber 18 so that the syringe neck will not become jammed.

The urine collection container 10 with buffered urine contains polyclonal labelled antibodies having a binding site contoured to the epitope structure and chemistry of the desired antigen. This antigen has been previously determined as being a marker for a specific type of cancer. The polyclonal antibodies are labelled with HRP (horseradish peroxidase), an enzyme that detoxifies hydrogen peroxide, $H_2O_2$, by converting it to water. HRP initiates this transformation when it gives hydrogen peroxide a pair of electrons. The enzyme subsequently collects these electrons from suitable donors. Thus the total color generated by peroxidase depends upon the relative rates of color generation and product inactivation of the enzyme. The antigen has epitopes which have a high affinity for the binding sites of the primary labelled antibody and immobilized antibody.

The principle of affinity chromatography requires that a successful separation of a biospecific ligand is available and that it can be chemically immobilized to a chromatographic bed material, the matrix. Numbers of methods well known in the art have been used to couple or immobilize antibodies to a variety of activated resins. Examples of immobilization techniques which exhibit variable linkage are those formed by the reaction of the reactive groups on the support with amino, thiol, hydroxyl, and carboxyl groups on the protein ligand. The selection of the ligand is influenced by two factors. First, the ligand should exhibit specific and reversible binding affinity for the substance to be purified and secondly it should have chemically modifiable groups which allow it to be attached to the matrix without destroying its binding activity. (Examples of such are Protein G Sepharose manufactured by Pharmacia, Hydrazide AvidGel Ax manufactured by BioProbe International, and Actigel-ALD manufactured by Sterogene Bioseparation Inc.)

An advantage to the use of Actigel-ALD is that it does not cross link proteins therefore allowing proteins to retain high bioactivity after their immobilization. Actigel-ALO SUPER FLOW also available from Sterogene Bioseparation Inc. permits a linear flow rate of up to 3000 cm/h which would fit nicely with the flow rates in the apparatus (approx 10-100 cm/min).

The resin beads 50 with matrix and primary ligand (in this case immobilized monoclonal antibody) having had flow contact with the filtered urine in buffered form from the addition of 200 mM Tris-HCL Buffer Solution, with $NaN_3$ manufactured by Pharmacia captures through antigen-antibody reaction with or immune reaction the specific ligand component carried by the urine namely, the complexed antigen/labelled antibody. It should be noted that labelled polyclonal antibody in solution has been previously added to the buffered urine.

In operation, the cytology cup 26 is removed from the shuttle container 12 before proceeding. A 10 cc syringe is used to draw up one ml of the Buffer Solution. Cap 27 is removed from the shuttle container 12 and end 20 is attached to the leur lock 22 of syringe barrel 34. The urine 100 is withdrawn from container 10 until the combined volume of urine/buffer prelabelled antibody solution is 10 cc with a pH of 8.8. The cytology cup 26 is attached to shuttle container end 21 and the urine buffer mixture is pushed by piston 34 through the shuttle container 12 and filter 28 of cytology cup 26 into a clean container. The cytology cup 26 is then removed from the shuttle.

Using a 3 cc syringe 1 cc of cytology fixative is injected into the disengaged cytology cup 26 and the cup is capped with a cap member not shown. The cytology specimen is then stable until further processing. The urine buffer mixture is drawn back up into the syringe 24 and set aside. The fluid is then discharged after incubation through the shuttle container into a discard container. At this point the cytology specimen can be reattached to the shuttle container 12 and placed in a box to be returned for cytological examination or cytological examination may be performed by the participating laboratory.

Figure 3:
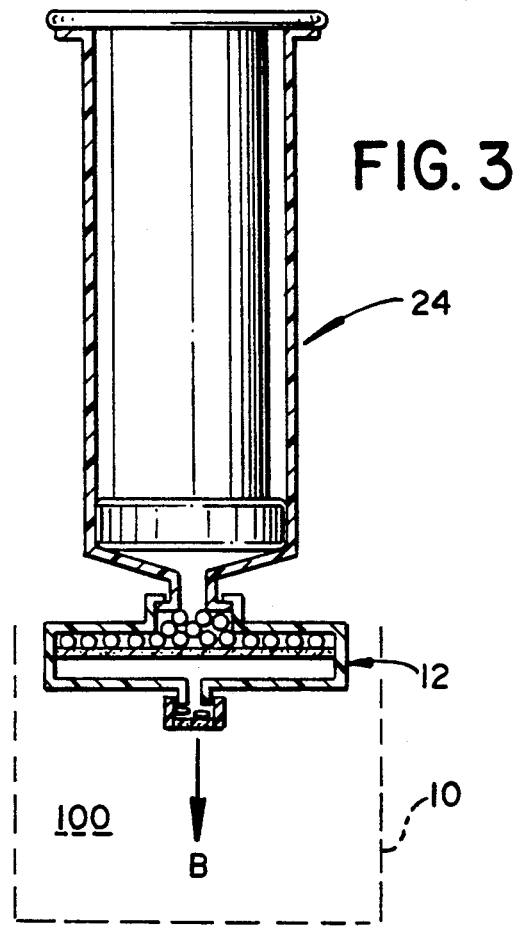
FIG. 3 is a cross sectional schematic view showing sequential movement of the syringe plunger in the opposite direction from that shown in FIG. 2 with the buffered urine being discharged from the syringe with direction of movement shown by arrow B and the immobilized antibody beads piled in one compartment of the shuttle container.
Figure 4:
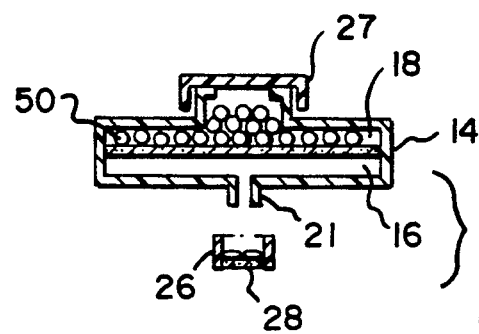
FIG. 4 is cross sectional schematic view of the shuttle apparatus shown in FIG. 1 with an exploded view of the cell collection cup.

When the specific cancer antigen is present in the urine testing sample 100, which is preferably a first morning voided urine, the antigen reacts with the labelled antibody to form a antigen/antibody complex The complexed antigen/antibody is captured by the immobilized antibody carried by beads 50 and thus remains in the housing chamber 18 as is clearly shown in FIG. 3. If there is an absence of the antigen in the specimen sample 100 the immobilized antibody on the beads 50 will remain unoccupied.

The buffered sample is drawn into the syringe and squirted out or inverted three to five times as desired to provide maximum fluid flow over the beads. The shuttle is then washed in the coloring reagent. After the urine has flowed over the beads 50 and deposited complexed antibodies on the immobilized antibodies, the bead bed is preferably soaked with ABTS solution. A hydrogen peroxide ($H_2O_2$) solution may be alternately placed on the bead bed when OPD or TMB or other dual substrate systems are used.

The color solution used on the bead matrix is preferably a substrate manufactured by Kirkegaard & Perry Labs under one of several acronyms, namely, ABTS (2,2'-azino-di-[3-ethylbenzthiazoline sulfonate (6)]; OPD (ortho-phenylene diamine); or TMB (tetramethylkbenzidine). In choosing the substrate, the sensitivity of the immunoassay is determined by the discrimination of the antibody reagents. When this occurs, the use of a more sensitive substrate serves only to proportionately increase the signal and the background. The result is more color but the same signal-to-noise ratio. Should the more sensitive substrate push the absorbence over the cutoff of the reader, the faster substrate may in fact reduce the signal-to-noise ratio.

The preferred color solution of the present invention is ABTS. The preferred ABTS substrate is a one-component substrate. The HRP label on the prelabelled antibody is turned by the ABTS to a blue-green color and there is no change in color or absorbence when the reaction is stopped with SDS (sodium dodecyl sulfate) at which time the color developed is read using a reflectometer. If the assay optimization indicates the sensitivity of the immunoassay is limited by the color generated by the HRP substrate then the more sensitive TMB substrate would give more color development without a corresponding increase in the background. Another advantage of the TMB substrate is that it often lowers the amount of reagents required for the immunoassay. TMB substrate is a two component liquid substrate and requires hydrogen peroxide. HRP converts TMB to a blue product. When the reaction is stopped by acidification, the TMB product becomes yellow. ODP is generally provided as a tablet that is dissolved in buffer at the time of use. HRP converts OPD to a yellow product which continues to oxidize into a brown precipitate. Upon acidification the OPD product becomes orange.

The bead bed matrix and immobilized ligand (in this case, immobilized antibody) captures the antigen/antibody complex through antigen/antibody reaction or immune reaction. The antibody in the complex as previously noted was provided labelled with coloring enzyme HRP. This labelling enzyme of the antibody reacts with the ABTS poured on the bead surface turing the surface of the bead into a blue green color. If there is an absence of the specific antigen in the specimen sample 100 the labelled antibodies will remain unoccupied and will not bind to the immobilized antibodies. The degree of color developed should correlate with the amount of labelled antibody/antigen complexes which in turn correlates with the amount of antigen present in the sample 100. The color developed on the beads is then read using a reflectometer as is well known in the art.

The present high affinity beads 50 can capture the complexed antigen/antibody present in 100 ml or even more of the sample, depending on the frequency of filling and emptying the syringe. This will result in $500\times$ fold increase in the amount of antigen being captured by the beads. Preferably the syringe is filled with urine allowing the beads to move freely into the barrel of the syringe for maximum fluid contact and mixing. The syringe is emptied and refilled three to five times for maximum concentration so that $1,000\times$ antigen concentrations from that previously obtainable can be obtained.

The specimen life of the buffered specimen is 6 months or longer under ordinary storage conditions after washing the beads with preservative solution e.g. 0.01% Sodium Agide (Bacteriostatic agents).

In the foregoing description, the invention has been described with reference to a particular preferred embodiment, although it is to be understood that specific details shown are merely illustrative, and the invention may be carried out in other ways without departing from the true spirit and scope of the following claims:

What is claimed is:

1. An apparatus for testing molecular components contained in a biological fluid and collecting cellular materials from the biological fluid comprising fluid transport means, a specimen treatment unit mounted to said fluid transport means comprising a housing defining a chamber with an inlet and outlet means, a filter means mounted in said housing chamber dividing said chamber into two compartments, said filter means allowing biological fluid taken from a biological fluid source to flow therethrough concentrating cellular materials in one chamber by preventing the flow of the cellular materials therethrough, ligand bead means contained in one of said compartments in said chamber on the fluid transport means side of said filter means which is adapted to capture designated ligands carried by said biological fluid, and a cellular material collection cup mounted to said housing in fluid communication with said compartment on the fluid source side of said filter.

2. A method of testing for predetermined molecular bodies in a body fluid specimen comprising the steps of:
   a. collecting body fluid into a container;
   b. adding labelled antibodies to the body fluid so that said labelled antibodies complex with specific antigen contained in the body fluid;
   c. passing the body fluid through a treatment container holding an immobilized antibody bead means so that said body fluid contacts the bead means, the container being provided with a filter means which prevents the flow of bead means to the body fluid collection container and cellular sediments into a tubular apparatus while permitting the flow of bead means into said tubular apparatus communicating with the treatment container; and
   d. treating the immobilized antibody bead means so that designated captured antigen and their complexed labelled antibodies are reacted to obtain a cancer indicator test result.

3. A method of testing for predetermined molecular bodies in a fluid specimen comprising the steps of:
   a. collecting fluid into a container;
   b. adding labelled ligands to the fluid so that said labelled ligands complex with specific molecular indicators contained in the fluid;
   c. transporting the fluid from the fluid collection container through a treatment container via a pump apparatus, said treatment container holding a ligand capture means so that said fluid contacts the capture means, the treatment container being provided with a filter means which prevents the flow of capture means to the fluid collection container while permitting the flow of capture means into said pump apparatus, said filter means also preventing flow of suspended sediments into said pump apparatus which is in fluid communication with the treatment container; and
   d. treating the capture means so that designated captured molecular indicators and their complexed labelled ligands are reacted to determine the presence of a specific molecular structure.

* * * * *